United States Patent [19]

Gokel

[11] Patent Number: 4,783,528

[45] Date of Patent: Nov. 8, 1988

[54] STEROIDAL LARIAT ETHERS

[75] Inventor: George W. Gokel, Miami, Fla.

[73] Assignee: University of Miami (Department of Chemistry)

[21] Appl. No.: 58,774

[22] Filed: Jun. 5, 1987

[51] Int. Cl.[4] .......................... A61K 31/56; C07J 9/00
[52] U.S. Cl. ..................................... 540/113; 540/116
[58] Field of Search ................................ 540/113, 116

[56] References Cited

U.S. PATENT DOCUMENTS 4,031,111  6/1977  Pedersen et al. ................ 260/340.3
4,436,664  3/1984  Gokel ............................. 260/330.6
4,474,963  10/1984 Gokel ................................. 546/178
4,597,903  7/1986  Gokel et al. ................... 260/330.6

Primary Examiner—Leonard Schenkman
Assistant Examiner—Joseph A. Lipovsky
Attorney, Agent, or Firm—Joseph P. Nigon

[57] ABSTRACT

A new class of macrocylic polyethers having a crown ether attached to a steroid by various connector units have been prepared. These novel structures have applications as ionophores and they form unique, nonionic vesicles (niosomes).

7 Claims, No Drawings

STEROIDAL LARIAT ETHERS

BACKGROUND OF THE INVENTION

The compounds of the instant invention are in the class of molecules that have been called "crown ethers". The crown ethers were originally named by Charles Pedersen who revealed in 1967 in a paper published in the *JOURNAL OF THE AMERICAN CHEMICAL SOCIETY* at volume 87, page 7071, that macrocyclic polyether compounds could bind cations. From the appearance of their molecular models, Pedersen said that the rings appeared to crown the cations when they complexed therewith. The systematic nomenclature for crown ethers is fairly complicated and the name crown has thus found very wide use.

Crown ether compounds are commonly named using a number-crown-number sequence. The first number identifies the total number of contiguous atoms which comprise the macroring. Crown is the informal family name and indicates the presence of repeating $CH_2CH_2O$ units. The second number designates how many heteroatoms are present in the macroring. A cycle of six ($-CH_2CH_2O-$) units would be called 18-crown-6.

The compounds of the instant invention also comprise the subclass ethers called the lariat ethers first described in Gokel, G. W.; Dishong, D. M.; Diamond, C. J.; *J. CHEM. SOC., CHEM. COMMUN.*, 1980, 1053. These are compounds which have a macroring bound to one or more pendant sidearms and are described in detail in U.S. Pat. No. 4,474,963 issued Oct. 2, 1984, U.S. Pat. No. 4,436,664 issued Mar. 3, 1984 to George W. Gokel and U.S. Pat. No. 4,597,903 issued to George W. Gokel and Vincent J. Gatto.

In the instant invention, we demonstrate structures having oxygen-or oxygen- and nitrogen-containing macrorings bound to chlesteryl or dihydrocholesteryl residues. The steriodal sidearms are attached either at carbon on the macroring 2-position of an all-oxygen ring or at the nitrogen of an azamacrocycle. When the sidearm is attached at carbon, these structures are called carbon-pivot lariat ethers. When the sidearm is attached to the nitrogen atom, the structures are called nitrogen-pivot lariat ethers.

The macrocyclic polyether rings contain heteroatoms such as oxygen or nitrogen. As such, they are fairly polar residues. When bound through some sort of spacer or connector unit to a steroidal system, the overall character of the molecular is amphiphilic. The steroidal residue, which usually contains more than twenty-five carbons, is extremely lipophilic. In addition, the steroidal residue is large and nearly flat but slightly helical. The large number of carbon-hydrogen bonds in the steroid nucleus make it nonpolar or oleophilic (lipophilic) and thus insoluble in water under normal circumstances.

The steriodal nucleus can be attached to the macrocyclic polyether ring in several ways. The general approach is illustrated schematically below:

Attachment of a Steroid to a Macroring: Schematic Representation

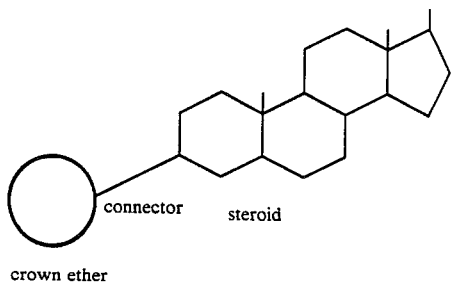

Macrorings.

The macrorings of interest in the present invention contain oxygen, nitrogen, or sulfur heteroatoms. The range of sizes we have surveyed in this work, as well as the work reported in Dishong, D. M.; Diamond, C. J.; Cinoman, M. I.; Gokel, G. W.; *J. AM. CHEM. SOC.* 1983, 105, 586., (a) Schultz, R. A.; Dishong, D. M.; Gokel, G. W.; *J. AM. CHEM. SOC.* 1982 104, 625, and Schultz R. A.; White, B. D.; Dishong, D. M.; Arnold, K. A.; Gokel, G. W.; *J. AM. CHEM. SOC.* 1985, 107, 6659, as well as in the patents and publications listed above, include 12–24 members. Our most detailed studies have been with 15- and 18-membered crown ethers containing all oxygen heteroatoms, or one or two nitrogen atoms. We studied systems containing three nitrogen atoms in the macroring as well.

Steroid Subunits.

In the present case, we exemplify both the cholesteryl and dihydrocholesteryl (cholestanyl) steroid nulclei. Innumerable, closely related steroids are known and these could be exchanged for the present systems. Indeed, the steroid nuclei illustrated in Scheme 1 could all be attached to a macrocycle by the means described in detail hereinafter. The compounds which would be useful in the present invention are all those having the fused 6-6-6-5 ring (ABCD) steroid nucleus and having a point of attachment available in one of the rings. Steroids are commonly oxidized at the 3- and 17- positions and these positions thus represent especially attractive synthetic access. Attachment of the macroring at either the B or C ring, rather than the A or D ring would result in a compound having a broader and flatter shape than the compounds described experimentally herein.

SCHEME 1

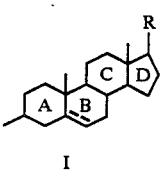

I

R = straight or branched chain alkyl groups having from 1-12 carbon atoms. Steroid B ring may be saturated or unsaturated as indicated by dotted line. Point of attachment is A ring, 3-position.

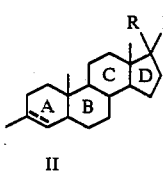

II

R and R' are straight or branched chain alkyl groups having from 1-12 carbon atoms or one, but not both, may be N, O or S, substituted by alkyl groups as above. Steroid B ring is either saturated or unsaturated as indicated by dotted line.

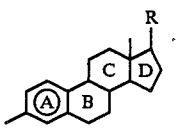

III

-continued
A ring is aromatic; otherwise as in I above.

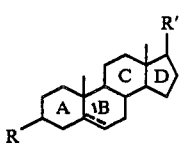

IV

R' is the point of attachment in this case.
R is a straight or branched chain aliphatic residue having 1-12 carbon atoms or may be part of an ether or amine.

Points of Attachment.

In the class of molecules disclosed herein, there are two points of attachment which must be considered. These are: attachment of the spacer (1) to the steroid and (2) to the macroring. If the macroring contains only oxygen donor atoms or a combination of oxygen and sulfur donors, attachment is at carbon since the specified heteroatoms are normally divalent. Although attachment to either sulfur or oxygen could, in principle, be made by formation of a sulfonium or oxonium salt, such species are relatively unstable, especially the latter.

When attachment is made to carbon of a macroring, it must involve an additional carbon. This is because both carbon atoms in the $-CH_2-CH_2-O-$macroring subunit are adjacent to oxygen. If heteroatoms were attached to either carbon, a hydrolytically unstable species would result. For example, direct attachment of oxygen to a macroring carbon would convert the $-CH_2-O-$unit to a $-CH(O)_2-$unit. Carbon is thus converted from the relatively stable ether state to the hydrolytically unstable acetal state. By using an additional carbon, the macroring unit becomes $-CH_2-CH(CH_2X)-O-$. The carbon which is part of the $-CH_2X$ unit is no longer adjacent to a heteroatom and forms a simple ether, etc. when substituted. Likewise, a single methylene group bridging a steroidal oxygen and crown ether oxygen would create an unstable acetal.

We demonstrate herein a variety of hydroxy acid connector residues. We have prepared both carbamate and acetic acid derivatives of the various steroids and macrocycles. Although, in principle, any length of spacer and any functionality may be used in the attachment of the macroring to the steroid, we have prepared a limited number of examples. We believe these completely exemplify the process and anyone skilled in the art can easily envision other such connectors. Several possible additional connectors are the following: $-CH_2-CH_2-$, $-CH_2CH_2CH_2-$, $-CH_2CH_2CH_2CH_2-$, $-CH_2-CO-CH_2-$, $-CH_2-CH_2-CO-$; simple aromatic rings may be used in which the points of attachment are the respective methylene groups of ortho-, meta-, or preferably para-xylene. Additional spacers and means of contact will become apparent from a reading hereinafter.

Two distinct, but related, concepts motivated the synthesis of these steroidal lariat ethers. First, it was our intention to prepare compounds which would have a cation binding structure or head group with cation binding affinity attached to a large, flat lipophilic surface. The steroidal surface fits these criteria and is well known to cause association with concurrent formation of liquid crystalline arrays. An important part of the original concept was that such a liquid crystalline array may have organized hydrocarbon surfaces which would, in turn, orient the macrorings into a channel. Such an oriented cation binding channel might allow for the construction of a molecular wire. A cation bound sequentially by one macroring after the other would be a cation conducting channel or wire.

A further aspect of this initial concept was that because steroids, and cholesterol derivatives in particular, are known to form a helical array in the liquid crystalline domain, our thought was that these supramolecular arrays might be thermally sensitive. Since liquid crystals change helicity with temperature and therefore change their orientation with respect to each other, we thought this would force the pendant macrorings to change their orientations. If a cation needed a direct channel to be conducted through it, then changing the temperature and therefore the orientation of the channel would force the cation to be at least partially blocked. The concept was then of a thermally attenuated macrocyclic polyether cation channel.

The second concept which motivated our synthesis of these molecules had to do with the possibility of forming nonionic Langmuir-Blodgett films, nonionic micelles, or nonionic vesicles. In the latter case, especially, there is almost nothing known about nonionic vesicles. We have successfully prepared the first examples of nonionic vesicles based on steroidal lariat ethers.

DETAILED DESCRIPTION OF THE INVENTION

The compounds of the instant invention can be conceptualized in three distinct parts. The first part is a macrocyclic polyether, aminoether, or thioether ring. These are macrocyclic structures containing carbon, oxygen, nitrogen, and/or sulfur atoms. The oxygen, nitrogen, or sulfur heteroatoms are normally separated by two carbon units, although other distances are possible. In particular, in derivatives containing nitrogen, two nitrogens are often separated by three carbons rather than two.

Synthesis.

We considered several different methods for attaching the cholesteryl units to the macrocycle. Our own experimental program presented two obvious variants in macrocycles: The carbon-[5] and nitrogen-pivot[6] lariat ether systems. From the mechanical point of view, a carbon-pivot, steriodal lariat ether offers a chemically stable species having a readily synthesized linkage.

Two approaches to cholestanyl lariat ether 3 involve alkylation of the preformed macrocycle. In one case, the cholestanyl tosylate might serve as the alkylating agent; in the other, the crown tosylate would play this role. We anticipated that a secondary cyclohexyl tosylate derived from cholestanol (dihydrocholesterol) would eliminate rather than substitute. We attempted the second route but 2-tosyloxymethyl-15-crown-5 did, indeed, undergo elimination rather than substitution.

The synthesis of the carbon-pivot, cholestanyl lariat ether 3 was conducted as shown in Scheme 1, which follows. Commercially available 3-beta-cholestanol (dihydrocholesterol) was O-allylated under phase transfer catalytic conditions to give the crystalline allyl cholestanyl ether, 1, in 72% yield. Catalytic bis(hydroxylation) using $OsO_4$ and N-methylmorpholine-N-oxide, afforded the crystalline diol, 2, in 80% yield. Reaction of the dialkoxide derived from 2 (NaH, THF) with tetraethylene glycol ditosylate afforded, after chromatography, cholestanyl lariat ether 3 in 10% yield as a glassy solid, mp 61°-63° C.

SCHEME 2 chloroacetate, and Na$_2$CO$_3$ were heated in MeCN for 24 hours. Cholesteryl crown 4 was obtained in 68% yield (mp 85°-86° C.) after workup and chromatography.

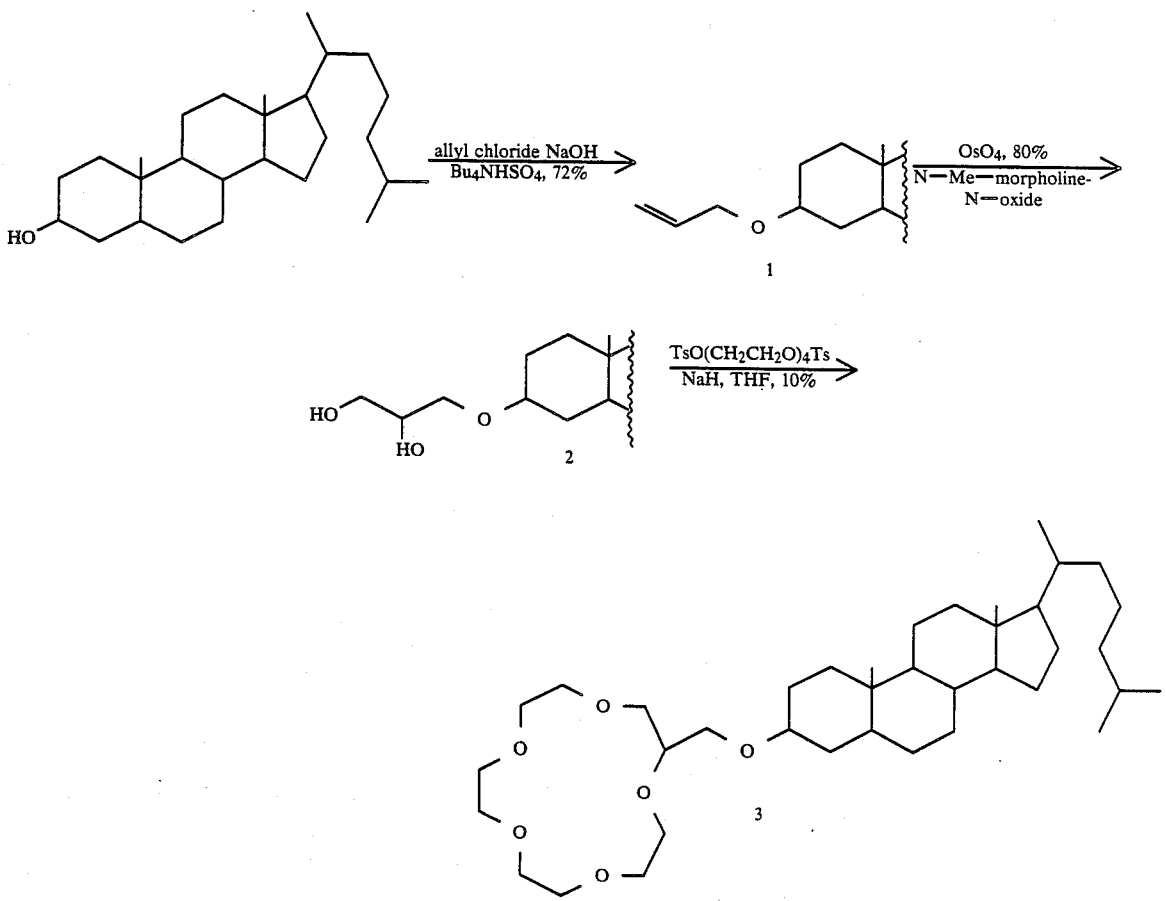

Azacrowns differ from the parent macrocycles in a variety of ways, most notably in basicity. Lariat ethers based on azacrown macrocycles in which the sidearm is attached at the nitrogen atom, are generally more flexible than their all-oxygen counterparts.

The direct analog of 3 in the azacrown series would involve a N—CH$_2$—O linkage between macroring and sidearm. Such a linkage is hydrolytically unstable and the synthesis of this analog was not attempted.

The corresponding N-substituted, aza-15-crown-5 derivative was prepared in two steps from dihydrocholesterol. Chloroacetic acid was heated for a week with a slight excess of dihydrocholesterol in anhydrous benzene using a Dean-Stark trap. Chromatography over silica gel G afforded the alkoxyacetic acid derivative as shiny, sheet-like crystals. Aza-15-crown-5, cholesteryl The 15- (6) and 18-membered ring (7) analogs of 4 based on dihydrocholesterol, were prepared similarly. Cholestanyl (aza-15-crown-5) acetate, 6, was obtained as a white solid, mp 60°-61° C., in 67% yield. Likewise, 7, mp 53°-54° C., was obtained in 65% yield. The 15- (8) and 18-membered ring (9) derivatives having cholesterol linked to the azacrown by a carbamate residue were prepared in a single step from commercially available cholesteryl chloroformate and the appropriate azacrown. Both the 15- (8) and 18-membered ring (9) derivatives proved crystalline and they were isolated in 34% and 52% yields respectively. Recrystallization of 8 from anhydrous EtOH afforded crystals suitable for X-ray analysis.

SCHEME 3

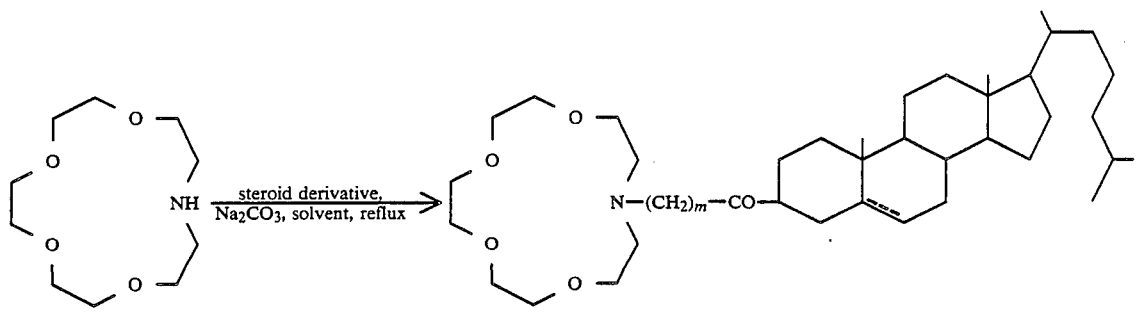

```
4  n = 1, m = 1, unsaturated
5  n = 2, m = 1, unsaturated
6  n = 1, m = 1, saturated
7  n = 2, m = 1, saturated
8  n = 1, m = 0, unsaturated
9  n = 2, m = 0, unsaturated
```

Cation binding by steroidal lariat ethers.

Cation binding constants (log $K_S$) in anhydrous methanol solution determined at 25° C. for the steroidal crown ethers prepared as part of this study are recorded in Table I. Several of these crown ethers are not true lariat ethers because they lack donor groups in the sidearms. As a result, only the macroring itself is expected to provide cation binding sites. Previous studies of the equilibrium stability constants for the reaction: ligand $+ M^+ =$ complex, having shown that 18-membered rings are generally stronger binders than analogous 15-membered ring compounds. The magnitude of $K_S$ with such metals as $Na^+$ or $K^+$ is generally reduced in related systems when an oxygen donor is replaced by nitrogen. In compounds 8 and 9, not only has the poorer donor atom replaced oxygen, its donicity has been reduced by converting it from $sp^3$ to $sp^2$ hybridization.

TABLE I

Cation Binding Constants for Sterodal Lariat Ethers[a]

| Cpd. No. | Ring Size | Pivot Atom | Linkage | Sidearm | $Na^+$ | $K^+$ |
|---|---|---|---|---|---|---|
| 3 | 15 | C | ether | dihydro-cholesteryl | — | — |
| 4 | 15 | N | acetate | cholesteryl | 4.10 | 4.03 |
| 5 | 18 | N | acetate | cholesteryl | 4.56 | 5.75 |
| 6 | 15 | N | acetate | dihydro-cholesteryl | 4.12 | 4.03 |
| 7 | 18 | N | acetate | cholesteryl | 4.58 | 5.78 |
| 8 | 15 | N | carbamate | cholesteryl | <1.5 | <1.5 |
| 9 | 18 | N | carbamate | cholesteryl | 2.07 | 1.78 |

Notes.
[a]Binding constants determined in anhydrous methanol solution at 25° C. as described in the articles by Dishong et al., and Schultz et al. referred to above.

Notes. a. Binding constants determined in anhydrous methanol solution at 25° C. as described in the articles by Dishong et al., and Schultz et al. referred to above.

FIG. 1. Structure of 8.

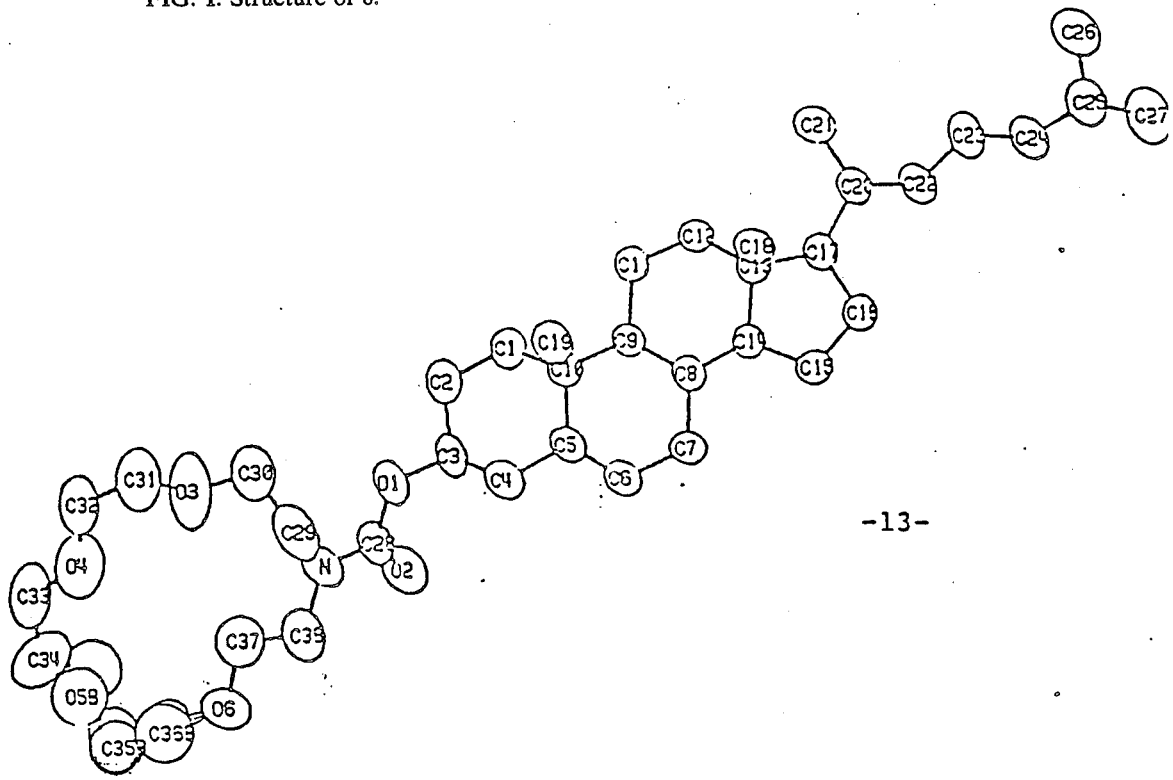

The binding constant, usually referred to as $K_S$, is the equilibrium constant for the reaction: lariat ether + cation $\rightleftharpoons$ complex. The values in the table are expressed as decadic ($\log_{10}$) logarithms. Thus, a value of 4.10 corresponds to an equilibrium constant favoring complexation by 12,600.

Structure of 8.

The existence of steroidal lariat ethers, the compounds of the instant invention, was demonstrated unequivocally by X-ray crystallographic analysis. The structure of cholesteryl lariat 8 is shown in FIG. 1. The most interesting feature of the structure is the ring conformation. The structural features of the cholesteryl sidearm are typical of known steroid systems. In a search of the Cambridge Crystal Files, no carbamate esters were found but even so, the distances, angles, and torsion angles of the ester linkage are similar to those reported for twenty one carboxylate esters. The cholesteryl fragment of 8 is identical to those reported for other cholesteryl esters. Detailed comparisons of structural parameters are difficult because of high R-factors usually associated with cholesteryl structures. In fact, the structure of 8 has a low R-factor when compared to cholesteryl ester structures.

Uncomplexed 18-membered ring crown ether compounds containing only oxygen and nitrogen heteroatoms generally adopt the extended conformation first demonstrated by Dunitz for uncomplex 18-crown-6. Dunitz, D. J.; Dobler, M.; Seiler, P.; Phizackerley, R. P.; *ACTA CRYSTALLOGR. SEC. B.*, 1974, B30, 2739.

The exceptions are diaza-18-crown-6 as reported in Herzog, M.; Weiss, R.; *BULL. SOC. CHIM, FR.* 1972, 549. and triaza-18-crown-6. The latter structure is known from our own work and is unpublished. 4,7-Dithia-15-crown-5 appears to be dominated by the presence of the sulfur atoms. Both sulfur atoms are turned outward and away from the ring. Because of this, the normal staggered arrangement for the X—CH$_2$—CH$_2$—X linkages is found only between O4 and O5 in this compound. Indeed, the two sulfur atoms turn outward in the 12- and 15-membered ring dithiamacrocycles.

Structural details of the crown ring in the cholesteryl compound are less certain because of the disorder in atoms O5, C35, and C36. However, there are some features that are quite clear. Torsion angles about the C—C bonds in the crown are either g+ or g−, except C37–C38, which is a. The intra-annular void of the ring is partly filled by C37, a methylene group. In general, the ring is more compressed in order to fill the cavity. The torsion angles about C31-O3, C32-O4, C33-O4, and C36-O6 are anti, but the torsion angles about C30-O3, C38-N and N-C29 are anticlinal (116.0, −119.0, and −117.1 respectively). The C-N torsion angles are expected to be different because the nitrogen atom is amidic.

SUMMARY OF THE INVENTION

Synthetic access to a new class of steroidal lariat ethers is presented. These include carbon- and nitrogen-pivot systems and both 15- and 18-membered ring systems. These compounds bind cations such as Na$^+$ and K$^+$. They also form non-ionic vesicles (niosomes). The X-ray crystal structure of aza-15-crown-5-CO-O-cholesteryl confirms its structure and shows the inward-turned ring methylene, characteristic of uncomplexed 18-membered ring crown ethers.

DETAILED DESCRIPTION OF THE INVENTION

The following examples are set forth in illustrate, but expressly not limit, the instant invention.

General Experimentation.

Melting points (Thomas-Hoover apparatus, open capillaries) are uncorrected. Infrared (IR) spectra were recorded on a Perkin-Elmer 281 spectrophotometer as neat samples unless otherwise noted. Spectral bands are reported in cm$^{-1}$ and calibrated against the 1601 cm$^{-1}$ band of polystyrene. Proton nuclear magnetic resonance ($^1$H-NMR) spectra were recorded at 60 MHz as ca. 15 wt.-% solutions in CDCl$_3$ unless otherwise specified. Chemical shifts are reported in parts per million (delta) downfield from internal Me$_4$Si, and are reported in the order: chemical shift, spin multiplicity (b=broad; s=singlet; d=doublet; t=triplet; q=quartet; m=multiplet), and integration. Combustion analyses (C, H, N) were performed by Atlantic Microlabs, Atlanta, Ga.

All reagents were the best grade commercially available and were used without further purification unless otherwise specified. Cholesterol, dihydrocholesterol (cholestanol), and cholesteryl chloroformate were purchased from Aldrich Chemical Company. All solvents were distilled prior to use and tetrahydrofuran (THF) was distilled from LiAlH$_4$ or Na-benzophenone. Benzene and dioxane were dried by distillation from Na-benzophenone under a dry N$_2$ atmosphere immediately before use. N,N-Dimethylformamide (DMF) was dried by distillation from CaO prior to use. Oven temperatures are given for bulb-to-bulb distillations conducted in a Kugelrohr apparatus. Preparative chromatographic columns were packed with MCB activated Al$_2$O$_3$ (80–325 mesh, chromatographic grade, AX-611) or Fluka silica gel 60 (70–230 mesh, chromatographic grade). Precoated sheets (aluminum oxide 60 F-254 neutral-Type E or silica gel 60 F-254) 0.2 mm thick were used for TLC analyses.

EXAMPLE 1

M-Benzylaza-15-crown-5. Benzyl chloride (557.0 g, 4.4 mol) was allowed to react with diethanolamine (420.0 g, 4.0 mol) to afford N-benzyldiethnolamine after vacuum distillation (609 g, 78%): bp 143°–145° C./0.1 torr. N-Benzylaza-15-crown-5 was prepared by cyclization of N-benzylidiethanolamine (195 g, 1.0 mol) with triethylene glycol ditosylate (458.0 g, 1.0 mol) as described in Freedman, H. H.; Dubois, R. A.; *TETRAHEDRON LETT.;* 1975, 3252. The crude mixture was chromatographed (Al$_2$O$_3$, hexanes) distilled (Kugelrohr, 125° C./0.1 torr) to give the macrocyclic polyether (142.0 g, 46%) as a colorless oil.

EXAMPLE 2

Aza-15-crown-5 was prepared by hydrogenolysis of N-benzylaza-15-crown-5, as described previously. The title compound (6.5 g, 98%, bp 76° C./0.05 torr.) was isolated as a colorless oil which solidified to a soft, white hygroscopic solid (mp 30°–32° C.).

EXAMPLE 3

N-Benzylaza-18-crown-6 was prepared as described above for the 15-membered ring analog, (see Example 1) except that cyclization was effected with tetraethylene glycol ditosylate (502.0 g, 1.0 mol). The crude mixture was chromatographed (Al$_2$O$_3$ hexanes) and distilled (Kugelrohr, 130° C./0.05 torr) to give N-benzylaza-18-crown-6 (140 g, 40%) as a colorless oil.

EXAMPLE 4

Aza-18-crown-6 was obtained by hydrogenolysis of N-benzylaza-18-crown-6 as described above (10.0 g, 98%, mp 49°-51° C., bp 125° C./0.25 torr).

EXAMPLE 5

3-beta-Cholesteryl Allyl Ether, 1. A solution of 3-beta-cholestanol (15.0g, 38.6 mmol), allyl chloride (118.5 g, 1.55 mol), 50% aqueous NaOH (15.0 g, 38.6 mmol) and tetra(n-butyl) ammonium bisulfate (TBAB) (3.0 g, 8.9 mmol) was heated at reflux temperature for 13 days. The mixture was cooled to room temperature, water (150 mL) and ether (50 mL) were added to dissolve the salts, and the phases were separated. The aqueous phase was extracted with Et$_2$O (3 x 100 mL). The organic extracts were combined and evaporated in vacuo. Chromatography on silica (200 g, 15-25% CH$_2$Cl$_2$ in hexane) gave 1 (10.1 g, 61%) as a white crystalline solid, mp 68°-69° C. $^1$H NMR (CDCl$_3$) 0.7-2.1 (m, 47 H steroid), 3.2-3.3 (m, broad, 1 H, CH—O), 4.0 (d, 2 H, CH$_2$ allyl), 5.02-5.24 (m, 2 H, C=CH$_2$), 5.6-6.2 (, 1 H, HC=C); IR (mineral oil) 2920 (s), 2840 (s), 1450, 1360, 1090, 915 cm$^{-1}$. Anal. Cald for C$_{30}$H$_{52}$O: C, 84.04; H, 12.22. Found C, 83.91; H, 12.15.

EXAMPLE 6

3-Cholestanyloxy-1,2-propanediol, 2. Compound 1 (5.0 g, 11.6 mmol), N-methylmorpholine-N-oxide (1.75 g, 13.0 mmol) and OsO$_4$ (5 mg, 0.02 mmol) in a solution of 10:3:1 t-butyl alcohol/THF/water (700 mL) was heated at reflux temperature for 3 days. The mixture was cooled to room temperature and concentrated in vacuo. Recrystallization (MeOH) afforded 2 (4.3 g, 80%) as a white crystalline solid (mp 102°-104° C.); $^1$H NMR (CDCl$_3$) 0.7-2.1 (m, 47 H, steroid(, 2.6-2.7 (m, 2H, OH), 3.2-3.3 (m, broad, 1 H, CH—O), 3.5-3.9 (m. 5 H. CH$_2$—CH—CH$_2$—O). When D$_2$O was added, the mulltiplet at 2.6-2.7 disappeared; IR (mineral oil): 3400 (s), 2910 (s), 2840 (s), 1450, 1360, 1100 cm$^{-1}$. Anal. Calcd for C$_{30}$H$_{54}$O$_3$: C, 77.87; 11.76. Found: C, 77.62; H, 11.70.

EXAMPLE 7

Cholestanyloxymethyl-15-crown-5, 3. Sodium hydride (50% dispersion in mineral oil, 940 mg, 39.0 mmol) was washed with hexanes (3×100 mL), suspended in THF (400 mL), and the mixture was brought to reflux. A mixture of compound 2 (9.0 g, 19.5 mmol) and tetraethylene glycol ditosylate (9.8 g, 19.5 mmol) in THF (175 mL) was added slowly during 1 hour. The mixture was cooled to room temperature, filtered, and evaporated in vacuo. Column chromatography (silica gel, 0–10% acetone:hexanes) afforded 3 (1.2 g, 10%) as a slightly yellow, glassy solid (mp 61°-63° C.): $^1$H NMR (CDCl$_3$) 0.7-2.1 (m, 47 H, steroid), 3.4-3.7 (m, 22H, CH$_2$—O and HC—O); IR (neat) 2920 (s), 2860 (s), 1470, 1300, 1120 cm$^{-1}$. Anal. Calcd for C$_{38}$H$_{68}$O$_6$: C, 73.50; H, 11.04. Found: C, 73.31; H 11.31 [α]$_D^{25}$=+8.53°(c=1.7, CHCl$_3$).

EXAMPLE 8

Cholesteryl chloroacetate. A solution of cholesterol (1.93 g, 5 mmol) and triethylamine (0.51 g, 5 mmol) in benzene (25 mL) was added dropwise to an 8°-10° C. solution of chloroacetyl chloride (0.57 g, 5 mmol) in benzene (20 mL). The solution was heated under reflux at 80° C. for 24 hours, cooled to room temperature and worked up. Recrystallization (absolute EtOH) afforded the title compound (1.53 g, 66%) as a white solid (mp 160°-161° C.).

EXAMPLE 9

Cholesteryl (4-aza-15-crown-5)acetate, 4. Cholesteryl chloroacetate (0.05 g, 1.1 mmol), aza-15-crown-5 (0.24 g, 1.1 mmol) and Na$_2$CO$_3$ (0.13 g, 1.2 mmol) were heated at reflux (115° C.) in butyronitrile (40 mL) for 72 hours. The mixture was cooled, filtered, and concentrated in vacuo. Column chromatography (silica gel, 5% 2-propanol/hexanes afforded pure 4 (0.48 g, 68%) as a white solid (mp 85°-86° C.): $^1$H NMR (CDCl$_3$) 0.58-2.65 (m, 43H, steroid), 2.93 (t, 4H, —CH$_2$—N—CH$_2$—), 3.40-3.93 (m, 18H, crown and —N—CH$_2$—C—O—), 4.36-4.86 (broad-s, 1H, CH—O—), 5.30 ppm (broad-s, 1H, C=CH). IR (CCl$_4$): 2990 (s), 2900 (s), 1740 (w), 1190 (s) cm$^{-1}$, [α]$_D^{25}$=−23.85° (c=2, CHCl$_3$); Anal.: calcd for C$_{39}$H$_{67}$NO$_6$=C, 72.49; H, 10.46. Found: C, 72.24; H, 10.54.

EXAMPLE 10

Cholesteryl (4-aza-18-crown-6) acetate, 5. Cholesteryl chloroacetate (0.69 g, 1.5 mmol), aza-18-crown-6 (0.40 g, 1.5 mmol) and Na$_2$Co$_3$ (0.19 g, 1.8 mmol) in butyronitrile (45 mL) were set to reflux (115° C.) during 60 hours. The reaction mixture was cooled to ambient temperature, filtered, and concentrated in vacuo. Column chromatorgrpahy (silica gel, MeOH/CH$_2$Cl$_2$) afforded 5 (0.65 g, 63%) as a waxy, slightly yellow solid, mp 66°-67° C. NMR: 0.57-2.57 (m, 43H, steroid), 2.97 (t, 4H, NCH$_2$), 3.37-3.87 (bs, 22H, crown and N—CH$_2$—CO), 4.27-4.97 (s, broad, 1H, CHO), 5.27-5.47 (bs, 1H, —CH=C). IR (CCl$_4$): 2980 (s), 2900 (s), 1740 (s), 1130 (s) cm$^{-1}$. [α]$_D^{25}$=−20.6°(c=2, CHCl$_3$). Anal. calcd for C$_{41}$H$_{71}$NO$_6$: C, 73.07; H, 10.61. Found, C, 73.37; H10.91.

EXAMPLE 11

Dihydrocholesteryl chloroacetate. A solution of dihydrocholesterol (1.94 g, 5 mmol) and triethylamine (0.51 g, 5 mmol) in benzene (25 mL) was added dropwise to and 8°-10° C. solution and was then heated at reflux (80° C.) for 24 hours, cooled to room temperature, and filtered. The solution was concentrated in vacuo, the residue was dissolved in CH$_2$Cl$_2$ (50 mL) and consecutively washed with 3N HCl (4×25 mL), 5% Na$_2$CO$_3$ solution (2×25 mL), and water (25 mL). The organic phase was dried (Na$_2$SO$_4$) and concentrated in vacuo. Recrystallization (absolute EtOH) afforded cholesteryl chloroacetate (1.5 g, 65%) as a white solid (mp 180°-181° C.). $^1$H NMR (CDCl$_3$) 0.66-2.16 (m, 46H, steriod), 3.97 (s, ClCh$_2$—CO$_2$—), 4.43-4.97 ppm (s, broad, 1H, CH—O—). IR (CCl$_4$): 2985 (s), 1750 (s), 1185 (s) cm$^{-1}$. This compound was used directly in the next step.

EXAMPLE 12

Cholestanyl (4-aza-15-crown-5) acetate, 6. Dihydrocholesteryl chloroacetate (0.50 g, 1.1 mmol), aza-15-crown-5 (0.24 g, 1.1 mmol) and Na$_2$CO$_3$ (0.13 g, 1.2 mmol) were heated in butyronitrile (40 mL) at reflux 115° C.) for 72 hours. The mixture was cooled to room temperature, filtered, and concentrated in vacu. Column chromatography (silica gel, 5% 2-propanol/hexanes) afforded pure 5, (0.48, 67%) as a white solid (mp 60°-61° C.) $^1$H NMR (CDCl$_3$): 0.47-2.23 (m, 46H, steroid 2.92 (t, 4H, —CH$_2$—N—CH$_2$—) 3.33-3.83 (m, 18H, crown and —N—CH$_2$—CO$_2$—), 4.27-4.96 ppm (broad-s, 1H, —CH—O—); IR (CCl$_4$): 2930 (s), 2900 (s), 1740 (w), 1190 (s) cm$^{-1}$; $[\alpha]_D^{25}$+12.10°(c=2, CHCl$_3$); Anal. calcd for C$_{39}$H$_{69}$NO$_6$: C, 72.27; H, 10.74. Found: C, 72.09; H, 10.74%.

EXAMPLE 13

Cholestanyl (4-aza-18-crown-6)acetate, 7. The procedure described above for the synthesis of 5 was followed and the title compound was obtained (0.18 g, 65%) as a waxy, slightly yellow solid, mp 55°-56° C. NMR: 0.47-1.97 (m, 46H, steroid); 2.93 (t, 4H, NCH$_2$); 3.37-3.38 (m, 22H, crown and N—CH$_2$—CO); 4.30-4.87 (bs, 1H, CHO). IR (CCl$_4$): 2940 (s) 2900 (s), 1740 (s), 1150 (s), cm$^{-1}$. $[\alpha]_D^{25}$+9.4 degrees (c=2, CHCl$_3$). Anal. calcd for C$_{41}$H$_{73}$NO$_6$:C, 72.86; H, 10.88. Found: C. 73.16; H, 11.18.

EXAMPLE 14

N-(Cholesteryloxycarbonyl)aza-15-crown-5, 8. Aza-15-crown-5 (2.0 g, 9.0 mmol), Et$_3$N (1.4 g, 14.0 mmol) in DMF (50 mL) were heated to ca. 90° C. Cholesteryl chloroformate (3.6 g. 8.0 mmol) was added and the temperature was maintained at ca. 90° C. for 48 h. The mixture was cooled to room temperature, filtered, and concentrated in vacuo. Column chromatography (silica gel, 5% EtOAc/CHCl$_3$) followed by recrystallization (absolute EtOH) afforded pure 8 (2.0 g, 34%) as a white crystalline solid (mp 96°-98° C.): $^1$H NMR (CDCl$_3$) 1.5 (m, 44H, steroid), 3.63 (m, 20H, O—CH$_2$—CH$_2$—O and CH$_2$—N—CH$_2$), 5.30 (dd, 1H, C=CH); IR (KBr): 2940, 1705, 1230, 1160, 1130, cm$^{-1}$. Anal. Calcd for C$_{38}$H$_{65}$NO$_6$: C, 72.62; H, 10.22; N, 2.19. Found: C, 72.90; H, 10.50; N, 2.00. Crystals for X-ray analysis: 8 (1.0 g) was recrystallized from absolute EtOH (20 mL) to afford needles suitable for X-ray analysis.

EXAMPLE 15

N-(Cholesteryloxycarbonyl)aza-18-crown-6, 9. Aza-18-crown-6 (2.0 g, 8.0 mmol), Et$_3$N (1.4 g, 14.0 mmol) and DMF (50 mL) were heated to ca. 90° C. for 48 hours. The mixture was cooled to room temperature, filtered, and concentrated in vacuo. Column chromatography (silica gel, 5% EtOAc/CHCl$_3$) followed by recrystallization (absolute EtOH) afforded 9 (2.75 g, 52%) as a white solid, mp 82°-84° C.): $^1$H NMR (CDCl$_3$) 1.50 (m, 44H, steroid), 3.63 (m, 24 H, O—CH$_2$—C—and CH$_2$—N—CH$_2$), 5.30 (dd, 1 H, C=CH); IR (KBr) 2940, 1705, 1470, 1380, 1160, 1130 cm$^{-1}$. Anal. Calcd for C$_{40}$H$_{69}$NO$_7$: C, 71.09; H, 10.29; N, 2.07. Found: C, 70.97; H, 10.20; N, 2.14.

We claim:
1. Cholestanyloxymethyl-15-crown-5.
2. Cholesteryl (4-aza-15-crown-5)acetate.
3. Cholesteryl (4-aza-18-crown-6) acetate.
4. Cholestanyl (4-aza-15-crown-5)acetate.
5. Cholestanyl (4-aza-18-crown-6)acetate.
6. N-(Cholesteryloxycarbonyl)aza-15-crown-5.
7. N-(Cholesteryloxycarbonyl)aza-18-crown-6.

* * * * *